United States Patent [19]

Suzuki et al.

[11] 4,069,235
[45] Jan. 17, 1978

[54] METHOD FOR MANUFACTURE OF POLY-FATTY ACIDS

[75] Inventors: Osamu Suzuki, Yokohama; Keizo Tanabe, Tokyo; Tetsutaro Hashimoto, Urawa, all of Japan

[73] Assignee: Agency of Industrial Science & Technology, Tokyo, Japan

[21] Appl. No.: 653,218

[22] Filed: Jan. 28, 1976

[30] Foreign Application Priority Data

Jan. 31, 1975 Japan ............................ 50-13703
Nov. 19, 1975 Japan ............................ 50-138198

[51] Int. Cl.² ............................................ C08H 3/00
[52] U.S. Cl. ............................... 260/407; 260/413
[58] Field of Search ....................... 260/407, 413 M; 252/435

[56] References Cited

U.S. PATENT DOCUMENTS

| | | | |
|---|---|---|---|
| 2,793,220 | 5/1957 | Barrett | 260/407 |
| 2,974,054 | 3/1961 | Beamesderfer | 252/435 X |
| 3,157,681 | 11/1964 | Fischer | 260/407 |
| 3,213,035 | 10/1965 | Morrell | 252/435 |
| 3,412,039 | 11/1968 | Miller | 260/407 X |
| 3,507,890 | 4/1970 | Dieckelmann | 260/407 |

*Primary Examiner*—Winston A. Douglas
*Assistant Examiner*—John F. Michling
*Attorney, Agent, or Firm*—Oblon, Fisher, Spivak, McClelland & Maier

[57] ABSTRACT

A poly-fatty acid is manufactured by continuously passing a higher unsaturated fatty acid, over a catalyst having phosphoric acid deposited on a synthetic silica-alumina carrier.

4 Claims, No Drawings

METHOD FOR MANUFACTURE OF POLY-FATTY ACIDS

BACKGROUND OF THE INVENTION

This invention relates to a method for manufacturing, in high yields, poly-fatty acids mainly in the form of a dimer or trimer or maleic anhydride-added fatty acids from a higher unsaturated fatty acid. Dimers and trimers of higher fatty acids such as, for example, linoleic acid and linolenic acid remain unfrozen even at low temperatures and retain high degrees of viscosity and, therefore, find utility in the production of paints, surface active agents, rustproofing oil additives, lubricating additives, synthetic high polymers, etc. For the manufacture of these polymers, there have been suggested various methods which effect the relevant polymerization reactions by use of a clay catalyst (U.S. Pat. No. 2,347,562), a lithium-containing clay catalyst (Japanese Patent Publication No. 8427/1965, U.S. application Ser. No. 205,099, filed June 25, 1962, abandoned), a clay catalyst stabilized with a lithium compound (Japanese Patent Publication No. 7477/1967, U.S. application Ser. No. 343,894, filed Feb. 10, 1964, abandoned), a synthetic lithium silicate-magnesium catalyst (Japanese Patent Publication No. 980/1966, U.S. application Ser. No. 367,920, filed May 14, 1964, U.S. Pat. No. 3,405,150), an activated terra alba or terra alba catalyst (Japanese Patent Publication No. 5130/1963) and other similar catalysts.

All the methods disclosed to date invariably involve batchwise operations in which unsaturated fatty acids as the raw material are thermally polymerized within pressurized closed vessels for from one to ten hours at temperatures in the range of from 180° to 300° C in the presence of 5 to 35%, based on said fatty acids, of catalysts. For these polymerization reactions, it is plain that use of a continuous operation is advantageous over that of a batchwise operation. Notwithstanding this fact, no effective continuous process has ever been proposed.

For use as coating compositions, products of addition of maleic anhydride to higher unsaturated fatty acids or to the esters of said acids have been known to excel in hydrophilicity, exhibit high penetrating power, adhere quickly to said substrates as wood and metals and, on desiccation, provide high coating strength, outstanding water resistance and durability (U.S. Pat. Nos. 2,188,882, 2,188,883 and 2,188,890). Besides, as resinous compositions, they are used in lacquers and varnishes to serve the purpose of improving the properties of lacquers and varnishes (British Pat. No. 500,348); they have also been demonstrated to serve as excellent base oils for water-soluble paints and to be usable as sizing agents for paper (British Pat. Nos. 500,349 and 500,350); and they serve as excellent rubber compositions and are known to find utility as dispersants for plastics (British Pat No. 500,351). As regards the manufacture of products of addition of maleic anhydride to higher unsaturated fatty acids or to the esters of said acids heretofore known, there have been suggested various methods which accomplish the addition by placing mixtures of higher unsaturated fatty acids or esters thereof with maleic anhydride in closed vessels kept under an increased pressure or normal pressure and heating the charges in the absence of a catalyst for a period of from one to ten hours at temperatures in the range of from 150° to 300° C (U.S. Pat. Nos. 2,188,882, 2,188,883 and 2,188,890 and British Pat. Nos. 500,348, 500,349 500,350 and 500,351). It has recently been established that activated terra alba accelerates the reaction of addition of maleic anhydride to linoleic acid and at the same time inhibits a secondary reaction (J. of Japan Oil Chemists Society, 24, 149 (1975)). All the methods heretofore suggested for the addition reaction invariably cause the reaction to be carried out batchwise, namely, by use of fixed vessels. It is only evident that for the purpose of such an addition reaction, use of a continuous operation proves to be advantageous over that of a batchwise operation. Notwithstanding this fact, no effective continuous process has ever been proposed.

An object of the present invention is to provide a method for manufacturing poly-fatty acids mainly in the form of dimers and trimers by continuously polymerizing fatty acids under normal pressure.

Another object of the present invention is to provide a method for continuously manufacturing maleic anhydride-added fatty acids.

SUMMARY OF THE INVENTION

To accomplish the objects described above according to the present invention, a method is provided which comprises passing a higher ethylenically unsaturated fatty acid of 8 to 22 carbon atoms, either alone or in combination with maleic anhydride, over a catalyst of phosphoric acid deposited on a synthetic silica-alumina carrier maintained in a temperature range of from 150° C to 330° C and thereby manufacturing a corresponding poly-fatty acid or maleic anhydride-added fatty acid continuously.

In the synthetic silica-alumina carrier, the weight ratio of the alumina component to silica component should fall within the range of from 0.3 to 1.0. Moreover the amount of phosphoric acid supported on this synthetic silica-alumina carrier is desirably in the range of from 0.1 to 2.0 milli-equivalent based on 1 g of silica-alumina.

DETAILED DESCRIPTION OF THE INVENTION

Higher unsaturated fatty acids which are usuable as the raw material in the present invention are normal-chained or branch-chained poly- or mono-ethylenically unsaturated fatty acids having 8 to 22 carbon atoms such as, for example, oleic acid, linoleic acid and linolenic acid or conjugate fatty acids such as, for example, α-and β-eleostearic acids. These fatty acids may process an alcoholic hydroxyl group. The method of the present invention can effectively be applied such as to ricinoleic acid and ricineraidic acid, for example. Furthermore, the method of this invention can advantageously be applied to mixtures of these fatty acids or to fatty acids derived from mixtures preponderantly consisting of said higher fatty acids such as, for example, tall oil, soybean oil, linseed oil, cotton seed oil, safflower oil, castor oil, tung oil and other similar oils.

Now, a description will be made about the catalyst to be used for the present invention. A catalyst having phosphoric acid deposited on a synthetically prepared silica-alumina carrier is used. A method generally employed for the synthesis of silica-alumina composite comprises the steps of mixing water glass and sulfuric acid under vigorous agitation in relative amounts to give an $SiO_2$ concentration in the range of from 3.5 to 6% for thereby producing a slightly acidic $SiO_2$ hydrogel in the form of slurry, adding to this slurry a solution of $Al_2(SO_4)_3$, causing the aluminum component thereof to precipitate in said $SiO_2$ hydrogel by the medium of aqua ammonia, filtering the resultant $SiO_2 \cdot Al_2O_3$ hydrogel and washing it clean of the adsorbed sodium with a dilute solution of $NH_4Cl$. This washing completes the synthesis of said composite. During the ageing of said $SiO_2$ and $SiO_2 \cdot Al_2O_3$ hydrogels, their respective porous structures and fine gel structures are adjusted as required.

The synthetic composite consists preponderantly of $SiO_2 \cdot Al_2O_3$ and additionally contains $Fe_2O_3$, $CaO$ and $MgO$ to some extent. In the composite for use in this invention, the weight ratio of alumina to silica is comparatively large. It is desirable to use a silica-alumina composite wherein said weight ratio falls in the range of from 0.3 to 1.0, preferably from 0.4 to 0.6.

Particularly desirable for the purpose of the present invention is a pure synthetic silica-alumina which is composed of 69 to 72% of $SiO_2$, 27 to 30% of $Al_2O_3$, not more than 1% of $Fe_2O_3$, not more than 1% of $CaO$ and not more than 1% of $MgO$ by weight ratio.

If said weight ratio of alumina to silica does not reach the lower limit 0.3, the reaction according to the method of this invention produces the poly-fatty acid or maleic anhydride-added fatty acid in a notably inferior yield. If the weight ratio fails to reach 0.4, said poly-fatty acid or maleic anhydride-added fatty acid is produced in a yield slightly inferior to the optimum yield attainable. If this weight ratio exceeds 0.6, the yield in which said poly-fatty acid or maleic anhydride-added fatty acid is produced is inferior to some extent. If it exceeds the upper limit 1.0, formation of said poly-fatty acid or maleic anhydride-added fatty acid is hardly observed. Even a pure synthetic silica-alumina catalyst does not prove advantageous if the silica content thereof is too large. For example, a silica-alumina composite composed of 72% of $SiO_2$, 21% of $Al_2O_3$, 1 to 3% of $Fe_2O_3$ and 1 to 3% of $MgO$ is similar in composition to a natural clay catalyst and, therefore, fails to give quite satisfactory results. The aforementioned synthetic silica-alumina composite having a high alumina content acts excellently as a catalyst for the polymerization of said higher unsaturated fatty acid and for the addition of maleic anhydride to said higher unsaturated fatty acid, without reference to its crystalline structure.

The activity of the catalyst to be used in this invention has some relation with the surface area of the catalyst: The activity tends to increase with the increasing surface area of the catalyst. In the production of the dimer of an unsaturated fatty acid, for example, the reaction involved proceeds smoothly at temperatures of from 200° to 250° C where the catalyst has a large surface area (of the order of from 300 to 240 m²/g), at temperatures of from 250° to 300° C where the catalyst has a medium surface area (of the order of from 240 to 10 m²/g) and at temperatures above 300° C where the catalyst has a small surface area (less than 10 m²/g) or it is in a gelled form.

For the method of this invention, said synthetic silica-alumina catalyst must be used in a state having phosphoric acid deposited thereon. If the polymerization of said higher unsaturated fatty acid or the addition of maleic anhydride to said higher unsaturated fatty acid is carried out by using, as the catalyst therefor, said synthetic silica-alumina in a form having no phosphoric acid deposited thereon, then part of the fatty acid reacts with calcium or magnesium contained in the catalyst and consequently produces a metal soap. This production of metal soap becomes particularly notable when the reaction temperature exceeds 200° C. The metal soap thus produced eventually covers the surface of the catalyst and degrades the activity of the catalyst. To preclude the degradation of catalytic activity by the metal soap and ensure smooth progress of the reaction, therefore, the reaction must be carried out at temperatures not exceeding 200° C. At such low temperatures, however, the yield in which the product aimed at is manufactured is low. The metal soap also poses a serious problem in that the service life of the catalyst is shortened thereby. The present invention overcomes this disadvantage by having phosphoric acid deposited on said synthetic silica-alumina composite. The amount of the phosphoric acid thus deposited on the composite falls in the range of from 0.1 to 2.0 milli-equivalent, preferably from 0.5 to 1.5 milli-equivalent, per g of said synthetic silica-alumina catalyst. In the course of the reaction, the phosphoric acid serves to inhibit the formation of metal soap to a notable extent.

If the amount of said phosphoric acid deposited on the synthetic silica-alumina catalyst does not reach the lower limit 0.1 milli-equivalent per g of synthetic silica-alumina, formation of the soap occurs conspicuously and the polymer or addition product is obtained in a notably inferior yield. The yield increases with the increasing amount of phosphoric acid deposited and reaches its peak when the amount falls in the range of from 0.5 to 1.5 milli-equivalent. If the amount of the deposited phosphoric acid exceeds the upper limit 1.5 milli-equivalent, however, the product undergoes decomposition and the yield is slightly degraded consequently. If the amount further increases to exceed 2.0 milli-equivalent, the decomposition of the product occurs so heavily as to degrade the yield to a great extent. The presence of metal soap can also be inhibited to an appreciable extent by the presence of methanol to exist within the reaction system. The extent of inhibition obtainable by use of methanol, however, is decidedly small compared with the inhibition attainable by the use of phosphoric acid in the present invention.

Now, the method of this invention will be described. A flow reaction tube is packed with said catalyst having phosphoric acid deposited on the synthetic silica-alumina carrier and the bed of catalyst is heated in advance to a prescribed temperature. The raw material is continuously passed through the reaction tube. If a higher fatty acid alone is used as the raw material, a corresponding dimer is mainly produced. When linoleic acid having a chemical structure, $CH_3(CH_2)_4CH=CH \cdot CH_2 \cdot CH=CH(CH_2)_7COOH$, is used as the higher fatty acid, the resultant main product is a Diels-Alder addition dimer having, for example a chemical structure,

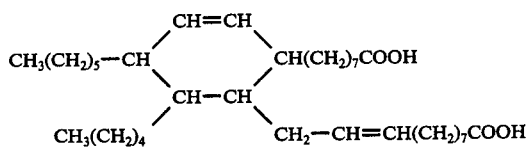

or a partially radical addition dimer having, for example, a chemical structure,

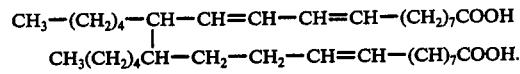

If a higher fatty acid is used in combination with maleic anhydride.

The relation between the raw material and the product in this case will be illustrated by way of example.

If linoleic acid having a chemical structure, $CH_3(CH_2)_4CH=CH-CH_2-CH=CH(CH_2)_7COOH$, or linolenic acid having a chemical structure, $CH_3(CH_2)_5CH-CH_2-CH=CH(CH_2)_7COOH$, is used as the higher fatty acid, the resultant addition product consists preponderantly of the Diels-Alder addition product of maleic acid having, for exmaple, a chemical structure,

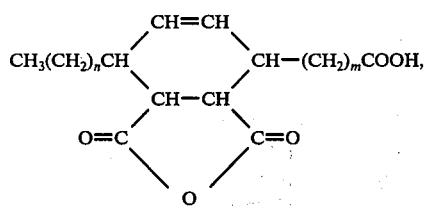

wherein $n$ is 7, 8 or 9 and the sum of $n$ and $m$ is 12. This relation has been confirmed by the inventors.

Although the reaction temperature is only required to fall in the range of from 150° to 330° C, it is desired to exceed at least 200° C for practical purposes. If the reaction temperature does not reach the lower limit 150° C, the activity of the catalyst is not sufficient and the yield is inferior. The activity gains in magnitude as the reaction temperature rises. If the reaction temperature exceeds the upper limit 330° C, however, the polymerization of a higher fatty acid gives rise to higher polymers other than dimer and trimer. If in this case, maleic anhydride is present in the reaction system, then the polymerization of the fatty acid itself proceeds excessively and the maleic anhydride itself undergoes decomposition to a serious extent, making it impossible to obtain the addition product aimed at. Thus, the reaction temperature must be limited to said range.

In the polymerization reaction which is carried out by the method of this invention, the activity of the catalyst is hardly degraded even when the packed bed of catalyst is swept by a total amount of the raw material more than ten times as large (by weight) as the catalyst. If the catalyst of the present invention is degraded in its activity, it can easily be regenerated by being submerged and washed in an organic solvent and subsequently calcined.

Since the method of this invention is of a flow type, it enjoys various advantages over the conventional batchwise method. For example, the polymer or addition product manufactured by the method of this invention can be recovered continuously in a state separated from the catalyst and, therefore, does not require any special treatment for separation of catalyst.

Owing to the adoption of a flow operation and the use of a highly active catalyst, the method of the present invention allows the reaction to be accomplished at a lower temperature in a shorter period of time. Thus, the extent of coloration which occurs on the product is small. The reaction, therefore, gives birth to a lightly yellow, clear product of high quality.

In the manufacture of the product of addition to a higher fatty acid, the product consists preponderantly of an addition product which consists of said fatty acid and maleic anhydride at a proportion of 1 : 1. In the conventional batchwise reaction performed in the absence of a catalyst, the product is mainly a combination of 1 : 1, 1 : 2 and 1 : 3 addition products. The method of the present invention, therefore, permits manufacture of a homogeneous product as compared with the conventional method.

When the method of the present invention is put to practice, it is desirable that the catalyst bed be deprived of its water component in advance by being heated under a current of nitrogen gas at a temperature about 10° C higher than the temperature of polymerization reaction.

The following working examples are further illustrative of the present invention. It should be understood that this invention is not limited to these examples.

EXAMPLE 1

A granular silica-alumina composite containing 70% of $SiO_2$, 29% of $Al_2O_3$, 0.7% of $Fe_2O_3$, 0.1% of CaO and 0.1% of MgO and, therefore, having the weight ratio of alumina to silica of 0.41, and measuring not less than 240 $m^2/g$ in surface area and 24 to 42 mesh in particle size was immersed in an aqueous solution of phosphoric acid and then dehydrated in a constant temperature bath at 150° C. Thus, catalysts having varying amount of phosphoric acid carried on said silica alumina composite as will be indicated later were prepared.

As the raw material, a fatty acid derived from safflower oil and possessed of the following composition was used.

| Component | Content (%) |
|---|---|
| Linoleic acid | 74.0 ~ 76.0 % |
| Oleic acid | 13.0 ~ 14.0 % |
| Linolenic acid | 1.0 ~ 2.0 % |
| Saturated fatty acid | 10.0 ~ 12.0 % |

For the reaction, there was used an apparatus comprised of a quartz tube serving as the reaction tube and measuring 50 cm in length and 1 cm in inside diameter, a ribbon heater (400 W) disposed to heat said reaction tube and a thermister attached intimately to the center portion of the tube proper to provide necessary temperature control. As accessories, the apparatus was provided with a reservoir for holding the higher fatty acid as the raw material and a preheater tube for connecting said raw material reservoir to the reactor tube. The preheater tube was a glass tube measuring 1 cm in inside diameter and 40 cm in length. The apparatus was so constructed that the raw material flowed out of the reservoir and ran through the preheater tube into the reaction tube via the upper portion thereof.

The reaction tube of said apparatus was packed with said catalyst. The amount of the catalyst thus deposited was 25 g.

Prior to the experiment, the reaction tube was thoroughly deprived of moisture by being heated in a current of nitrogen gas at a temperature more than 10° C higher than the reaction temperature for more than two hours. Then, the fatty acid of safflower oil was caused to flow out of the reservoir and run through the preheater tube into the reaction tube, with the reaction tube maintained at the reaction temperature and the preheater tube at a temperature 20° C lower than said reaction temperature, to produce a polymer.

The results of the experiment were as shown in Table 1 below.

Table 1

| Amount of phosphoric acid deposited per g of catalyst (milli-equivalent) | Reaction temperature (° C) | Yield (%) based on fatty acid | |
|---|---|---|---|
| | | Total polymer | Dimer |
| 0.25 | 170 | 47.8 | 45.2 |
| 0.5 | 140 | 36.0 | 31.5 |
| 0.5 | 150 | 40.7 | 37.3 |
| 0.5 | 160 | 46.2 | 45.0 |
| 0.5 | 170 | 51.6 | 46.2 |
| 0.5 | 180 | 52.0 | 48.6 |
| 1.0 | 150 | 53.0 | 49.2 |
| 1.0 | 170 | 58.7 | 53.5 |
| 1.0 | 190 | 28.5 | 51.8 |
| 1.0 | 210 | 60.0 | 51.6 |
| 1.0 | 230 | 65.5 | 51.3 |
| 1.0 | 250 | 71.5 | 38.8 |
| (0) | (160) | (38.8) | (30.5) |

In the experiment, the reaction time (duration of flow of the raw material) was 80 minutes.

EXAMPLE 2

The procedure of Example 1 was followed, except that the reaction involved use of a fatty acid from tall oil. The results of the experiment were as shown in Table 2 below.

On analysis, said fatty acid of tall oil was shown to have the following composition.

| Component | Content (%) |
|---|---|
| Oleic acid | 44.0 ~ 46.0 % |
| Linoleic acid | 37.0 ~ 38.0 % |
| Conjugate lineleic acid | 6.0 ~ 8.0 % |
| Saturated fatty acid | 5.0 ~ 6.0 % |
| Rhodinic acid | 1.8 % |

Table 2

| Amount of phosphoric acid deposited per g of catalyst (milli-equivalent) | Reaction temperature (° C) | Yield (%) based on fatty acid | |
|---|---|---|---|
| | | Total polymer | Dimer |
| 0.5 | 160 | 38.0 | 35.2 |
| 0.5 | 170 | 34.9 | 30.2 |
| 0.5 | 180 | 39.0 | 34.9 |
| 0.5 | 190 | 38.3 | 36.8 |
| 0.5 | 200 | 48.0 | 38.2 |
| 0.5 | 210 | 55.3 | 35.7 |
| 1.0 | 180 | 39.4 | 35.1 |
| 1.0 | 190 | 39.9 | 37.1 |
| 1.0 | 200 | 39.0 | 37.2 |
| 1.0 | 210 | 40.7 | 40.3 |
| 1.0 | 220 | 55.8 | 48.6 |
| 1.0 | 230 | 58.0 | 52.7 |
| 1.0 | 240 | 69.5 | 49.7 |
| 1.0 | 250 | 73.7 | 46.4 |

EXAMPLE 3

The fatty acid of tall oil was subjected to polymerization in the same apparatus as used in Example 1 by using a catalyst of phosphoric acid supported on the same high surface-area silica alumina catalyst as used in Example 1 at a ratio of 1 milli-equivalent of phosphoric acid per g of catalyst. In the experiment, the amounts of polymer and dimer produced were measured at indicated intervals to determine their changes due to change in the duration of continuous flow of the raw material. The results were as shown in Table 3. The yield of fatty acid given in the table represents the amount of the acid which flowed out during the indicated length of reaction time in the relevant lot.

By following the procedure of Example 1, the polymerization reaction was carried out at 230° C of reaction temperature and 210° C of preheating temperature, with the flow rate of fatty acid fixed at 5 ml/minute and the amount of catalyst at 25 g. The catalyst was prepared in the same manner as in Example 1.

Table 3

| Reaction time (minute) | Amount of fatty acid discharged (ml) | Yield computed on the basis of fatty acid (%) | |
|---|---|---|---|
| | | Total polymer | Dimer |
| 0 | 0 | 0 | 0 |
| 8 | 5 | 63.6 | 43.9 |
| 16 | 10 | 65.9 | 51.5 |
| 32 | 20 | 68.1 | 51.1 |
| 48 | 30 | 69.4 | 55.3 |
| 64 | 40 | 63.2 | 45.7 |
| 96 | 60 | 60.8 | 49.6 |
| 128 | 80 | 62.3 | 47.6 |
| 160 | 100 | 55.2 | 44.6 |
| 200 | 125 | 57.5 | 42.6 |
| 240 | 150 | 55.5 | 42.4 |
| 280 | 175 | 54.8 | 43.4 |
| 320 | 200 | 51.8 | 43.3 |

From the foregoing table, it is noted that even after the total amount of fatty acid discharged over a total of 320 minutes of reaction time reached 200 ml, the yield was degraded only slightly.

EXAMPLE 4

The high surface-area silica-alumina catalyst which had been used in the experiment of Example 3 and consequently degraded in activity was washed with methanol and thereafter regenerated by being heated in the atmosphere at about 650° C. In the presence of the regenerated catalyst, the fatty acid of tall oil was subjected to polymerization by repeating the same procedure. The results are shown in Table 4. The polymerization reaction was carried out under entirely the same conditions as those in Example 3.

Table 4

| Reaction time (minute) | Amount of fatty acid discharged (ml) | Yield computed on the basis of fatty acid (%) | |
|---|---|---|---|
| | | Total polymer | Dimer |
| 0 | 0 | 0 | 0 |
| 8 | 5 | 58.3 | 40.9 |
| 16 | 10 | 70.2 | 48.5 |
| 32 | 20 | 66.8 | 46.3 |
| 48 | 30 | 63.4 | 47.0 |
| 64 | 40 | 63.6 | 46.4 |
| 96 | 60 | 61.2 | 44.6 |
| 128 | 80 | 64.5 | 46.7 |
| 160 | 100 | 60.6 | 41.6 |
| 200 | 125 | 58.9 | 43.4 |
| 240 | 150 | 56.6 | 43.1 |
| 280 | 175 | 55.7 | 40.6 |
| 320 | 200 | 58.8 | 44.7 |

Comparison of the results given in Table 4 with those given in Table 3 permits one to appreciate that the catalyst had its activity completely regenerated by the treatment.

EXAMPLE 5

The fatty acid of safflower oil was subjected to polymerization in the presence of the supported catalyst having phosphoric acid adsorbed on the same high surface-area silica-alumina catalyst as used in Example 1 at a ratio of 1 milli-equivalent of said acid per g of catalyst. In the experiment, the amounts of polymer and dimer produced were measured at indicated intervals to determine their changes due to change in the duration of continuous flow of the raw material. The results are shown in Table 5.

By following the procedure of Example 1, the polymerization reaction was carried out at 230° C of reaction temperature and 210° C of preheating temperature, with the flow rate of fatty acid fixed at 5 ml/minute and the amount of catalyst at 25 g. The catalyst was prepared in the same manner as in Example 1.

Table 5

| Reaction time (minute) | Amount of fatty acid discharged (ml) | Yield computed on the basis of fatty acid (%) | |
|---|---|---|---|
| | | Total polymer | Dimer |
| 0 | 0 | 0 | 0 |
| 8 | 5 | 71.4 | 50.3 |
| 16 | 10 | 74.8 | 51.3 |
| 32 | 20 | 74.4 | 58.8 |
| 48 | 30 | 73.0 | 56.4 |
| 64 | 40 | 72.5 | 58.0 |
| 96 | 60 | 73.1 | 59.7 |
| 128 | 80 | 70.8 | 57.1 |
| 160 | 100 | 72.6 | 59.4 |
| 200 | 125 | 71.3 | 55.2 |
| 240 | 150 | 69.7 | 54.2 |
| 280 | 175 | 68.1 | 56.4 |
| 320 | 200 | 69.5 | 50.6 |

EXAMPLE 6

The fatty acid of castor oil taken as the raw material was subjected to polymerization by faithfully following the procedure of Example 1. The results of the experiment were as shown in Table 6.

On analysis, the fatty acid of castor oil was shown to have the following composition.

| Component | Content (% by weight) |
|---|---|
| Ricinoleic acid | 85.0 ~ 86.0 % |
| Linoleic acid | 6.0 ~ 7.0 % |
| Oleic acid | 4.0 ~ 5.0 % |
| Saturated acid | 2.0 ~ 3.0 % |

Table 6

| Amount of phosphoric acid supported on per g of SAH (milli-equivalent) | Reaction temperature (° C) | Yield computed on the basis of fatty acid (%) | |
|---|---|---|---|
| | | Total polymer | Dimer |
| 1.0 | 130 | 36.5 | 33.6 |
| 1.0 | 150 | 41.0 | 35.3 |
| 1.0 | 170 | 58.0 | 46.9 |
| 1.0 | 190 | 66.8 | 50.4 |
| 1.0 | 210 | 67.9 | 53.7 |
| 1.0 | 230 | 79.8 | 56.4 |
| 1.0 | 250 | 84.5 | 57.4 |

Table 6 shows that even from the fatty acid of castor oil composed preponderantly of ricinoleic acid, the poly-fatty acid could be produced in high yields.

EXAMPLE 7

The same fatty acid of castor oil as used in Example 6 was subjected to polymerization in the presence of a carried catalyst having phosphoric acid adsorbed on the same high surface-area silica-alumina catalyst as used in Example 1 at a ratio of 1 milli-equivalent of said acid per g of catalyst. In the experiment, the amounts of polymer and dimer produced were measured at indicated intervals to determine their changes due to change in the duration of continuous flow of the raw material. The results shown in Table 7.

By following the procedure of Example 1, the polymerization reaction was carried out at 230° C of reaction temperature and 210° C of preheating temperature, with the flow rate of fatty acid fixed at 5 ml/8 minutes and the amount of catalyst at 25 g.

Table 7

| Reaction time (minute) | Amount of fatty acid discharged (ml) | Yield computed on the basis of fatty acid (%) | |
|---|---|---|---|
| | | Total polymer | Dimer |
| 0 | 0 | 0 | 0 |
| 8 | 5 | 76.4 | 55.6 |
| 16 | 10 | 80.7 | 58.4 |
| 32 | 20 | 74.4 | 53.0 |
| 48 | 30 | 75.5 | 51.2 |
| 64 | 40 | 74.8 | 49.8 |
| 96 | 60 | 80.0 | 54.7 |
| 128 | 80 | 79.8 | 53.5 |
| 160 | 100 | 75.5 | 55.3 |
| 200 | 125 | 72.0 | 54.9 |
| 240 | 150 | 72.5 | 57.8 |
| 280 | 175 | 71.0 | 55.3 |
| 320 | 200 | 72.8 | 56.4 |

EXAMPLE 8

In the same apparatus as used in Example 1, a maleic anhydride-added fatty acid was manufactured by carrying out the procedure of Example 1 on the fatty acid of safflower oil having the same composition as shown in Example 1 plus maleic anhydride, in the presence of the same catalyst.

The fatty acid as the raw material and the reaction product were analyzed for composition by first methyl-esterifying them by an ordinary method and thereafter subjecting the resultant esterification products to gas chromatography at a constant temperature and at an elevated temperature (Suzuki: J. of Japan Oil Chemists Society, Vol. 20, p 492 (1971)).

In the experiment, the reaction was carried out to effect the addition of maleic anhydride to the fatty acid while the molar ratio of the fatty acid of safflower oil to maleic anhydride and the reaction temperature were changed. The results are shown in Table 8. The mixed solution of fatty acid and maleic anhydride was prepared by adding 10 ml of acetone to each 0.1 mol of maleic anhydride.

Table 8

| Fatty acid of safflower oil (mol) | Maleic anhydride (mol) | Reaction temperature (° C) | Yield of addition product based on fatty acid (% by weight) |
|---|---|---|---|
| 1.0 | 1.0 | 130 | 8.0 |
| 1.0 | 1.0 | 150 | 21.1 |
| 1.0 | 1.0 | 170 | 24.5 |
| 1.0 | 1.0 | 190 | 37.2 |
| 1.0 | 1.0 | 210 | 52.2 |
| 1.0 | 1.0 | 230 | 53.6 |
| 1.0 | 2.0 | 130 | 17.0 |
| 1.0 | 2.0 | 150 | 54.0 |
| 1.0 | 2.0 | 170 | 65.2 |
| 1.0 | 2.0 | 190 | 70.5 |
| 1.0 | 2.0 | 210 | 61.8 |
| 1.0 | 2.0 | 230 | 71.5 |

From Table 8, it is noted that the product of addition of maleic anhydride to the fatty acid of safflower oil was obtained in high yields, e.g. in a yield of not less than 50% at 210° C or over where the two acids were mixed equivoluminally and a yield of not less than 50% at 150° C where the molar ratio of the acids was 1 : 2. During the addition reaction, the amount of the poly-fatty acid (preponderantly of dimer) formed secondarily was found to be less than 4% by weight.

EXAMPLE 9

A mixed solution containing the fatty acid of safflower oil and maleic anhydride at a molar ratio of 1 : 1 was subjected to a continuous-flow reaction at 210° C in the presence of the same silica-alumina catalyst system as used in Example 8, by following the procedure of Example 8. The results were as shown in Table 9.

Table 9

| Reaction time (minute) | Amount discharged (ml) | Yield of addition product based on fatty acid of safflower oil (% by weight) |
|---|---|---|
| 0 | 0 | 0 |
| 8 | 5 | 39.8 |
| 16 | 10 | 62.8 |
| 32 | 20 | 76.9 |
| 48 | 30 | 61.7 |
| 64 | 40 | 61.0 |
| 96 | 60 | 70.1 |
| 128 | 80 | 58.9 |
| 160 | 100 | 57.2 |
| 200 | 125 | 56.1 |
| 240 | 150 | 56.1 |
| 280 | 175 | 42.8 |
| 320 | 200 | 46.7 |

From the foregoing table, it is noted that even after the total volume of the mixed solution of the fatty acid of safflower oil and maleic anhydride caused to flow through the 25-g catalyst bed had reached 200 ml, the activity of the catalyst was hardly impaired.

EXAMPLE 10

The high surface-area silica-alumina catalyst which had been used in the experiment of Example 9 was regenerated. In the presence of the regenerated catalyst, a mixture consisting of the fatty acid of safflower oil and maleic anhydride at a molar ratio of 1 :1 was subjected to a continuous-flow reaction under the same conditions (reaction temperature of 210° C) as those of Example 8, by following the procedure of Example 8. The results were as shown in Table 10.

Table 10

| Reaction time (minute) | Amount discharged (ml) | Yield of addition product based on fatty acid of safflower oil (% by weight) |
|---|---|---|
| 0 | 0 | 0 |
| 8 | 5 | 34.2 |
| 16 | 10 | 63.8 |
| 32 | 20 | 57.9 |
| 48 | 30 | 54.0 |
| 64 | 40 | 53.4 |
| 96 | 60 | 48.4 |
| 128 | 80 | 49.0 |
| 160 | 100 | 52.3 |
| 200 | 125 | 54.0 |

Comparison of the results shown in Table 10 with those given in Table 9 shows that the treatment provided thorough regeneration of the activity of the catalyst.

EXAMPLE 11

The same fatty acid of castor oil as used in Example 6 was subjected to addition of maleic anhydride in the presence of the same high surface-area pure synthetic silica-alumina catalyst as used in Example 8, by repeating the procedure of Example 8. The results were as shown in Table 11.

In the experiment, the reaction was carried out on varying lots which involved two kinds of specimens containing the fatty acid of castor oil and maleic anhydride at molar ratios of 1 : 1 and 1 : 2, with the reaction temperature varied as indicated.

Table 11

| Fatty acid of castor oil (mol) | Maleic anhydride (mol) | Reaction temperature (° C) | Yield of addition product based on fatty acid (% by weight) |
|---|---|---|---|
| 1.0 | 1.0 | 130 | 66.4 |
| 1.0 | 1.0 | 150 | 82.4 |
| 1.0 | 1.0 | 170 | 77.2 |
| 1.0 | 1.0 | 190 | 75.9 |
| 1.0 | 1.0 | 210 | 82.3 |
| 1.0 | 1.0 | 230 | 80.1 |
| 1.0 | 2.0 | 110 | 46.7 |
| 1.0 | 2.0 | 130 | 71.5 |
| 1.0 | 2.0 | 150 | 76.3 |

The results of Table 11 show that, compared with fatty acids from safflower oil and other oils which are composed preponderantly of linoleic acid, the fatty acid from castor oil which is composed preponderantly of ricinoleic acid proved to be a much more advantageous raw material for the production of the maleic anhydride addition product.

EXAMPLE 12

A mixed solution consisting of the fatty acid of castor oil (demonstrated by the experiment of Example 11 to provide the optimum results) and maleic anhydride at a molar ratio of 1 : 1 was subjected to a continuous-flow reaction at 150° C in the presence of a high surface-area silica-alumina catalyst, under the same conditions as involved in Example 1. The results were as shown in Table 12.

Table 12

| Reaction time (minute) | Amount discharged (ml) | Yield of addition product based on fatty acid of castor oil (% by weight) |
|---|---|---|
| 0 | 0 | 0 |
| 8 | 5 | 85.7 |
| 16 | 10 | 86.4 |
| 32 | 20 | 83.8 |
| 48 | 30 | 85.0 |
| 64 | 40 | 79.4 |
| 96 | 60 | 72.3 |
| 128 | 80 | 76.7 |
| 160 | 100 | 81.1 |
| 200 | 125 | 84.1 |
| 240 | 150 | 84.4 |

From Table 12, it is noted that even after the total volume of the mixed solution of the fatty acid of castor oil and maleic anhydride caused to flow through the 25 g catalyst bed had reached 150 ml, the activity of the catalyst was not impaired. Moreover, the average yields of the maleic anhydride-added fatty acid were considerably better than those of Table 8 obtained by using, as the raw material, the fatty acid of safflower oil. In this reaction, the reaction product had a high degree of viscosity, so that the flow rate of raw material was 5 ml/16 minutes or ½ of the ordinary flow rate.

What is claimed is:

1. A method for the manufacture of a poly-fatty acid, which comprises:
    continuously flowing and contacting at least one straight chain or branched chain ethylenically unsaturated fatty acid having a 8 to 22 carbon atoms with a synthetic silica-alumina catalyst having a composition of 69 to 72 weight % $SiO_2$, 27 to 30 weight % $Al_2O_3$ not more than 1 weight % $Fe_2O_3$, not more than 1 weight % CaO and not more than 1 weight % MgO and having phosphoric acid supported thereon in an amount of 0.1 to 2.0 milliequivalent per gram of said synthetic silica-alumina catalyst and maintaining the temperature of the reaction in a range of 150° C to 330° C, whereby said fatty acid is polymerized.

2. The method according to claim 1, wherein the ethylenically unsaturated fatty acid having 8 to 22 carbon atoms is selected from the group consisting of oleic acid, linoleic acid, linolenic acid, α-eleostearic acid, β-eleostearic acid, ricinoleic acid, ricinelaidic acid and fatty acids derived from tall oil, sybean oil, linseed oil, cotton seed oil, safflower oil, castor oil and tung oil.

3. The method according to claim 1, wherein the amount of phosphoric acid supported on the catalyst is from 0.5 to 1.5 milli-equivalent per g of silica-alumina.

4. The method according to claim 1, wherein the synthetic silica-alumina catalyst having phosphoric acid supported thereon is deprived of its moisture prior to contact with said fatty acid by heating said catalyst in a current of nitrogen gas at a temperature about 10° C higher than the temperature used for the production of the polyfatty acid.

* * * * *